United States Patent [19]

Schmidt et al.

[11] 4,095,972
[45] Jun. 20, 1978

[54] HERBICIDAL COMPOSITION OF PARTICULAR TRIAZINONE AND DIPHENYL ETHER

[75] Inventors: Robert Rudolf Schmidt, Cologne; Ludwig Eue, Leverkusen; Lothar Rohe, Wuppertal, all of Germany

[73] Assignee: Bayer Aktiengesellschaft, Leverkusen, Germany

[21] Appl. No.: 790,352

[22] Filed: Apr. 25, 1977

[30] Foreign Application Priority Data

May 8, 1976 Germany .............................. 2620371

[51] Int. Cl.² .............................................. A01N 9/02
[52] U.S. Cl. ........................................... 71/93; 71/105
[58] Field of Search ..................................... 71/93, 105

[56] References Cited

U.S. PATENT DOCUMENTS 3,954,829  5/1976  Rohe et al. ...................... 71/105 X
3,961,936  6/1976  Westphal et al. ...................... 71/93

*Primary Examiner*—Catherine L. Mills
*Attorney, Agent, or Firm*—Burgess, Dinklage & Sprung

[57] ABSTRACT

A herbicidal composition containing as active ingredients
(1)  4-amino-6-tert.-butyl-3-methylthio-1,2,4-triazin-5-one of the formula

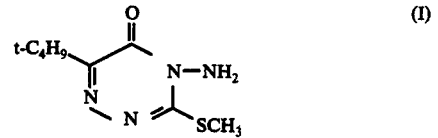

and (2) 2,6-dichloro-4-trifluoromethyl-4'-cyano-diphenyl ether of the formula

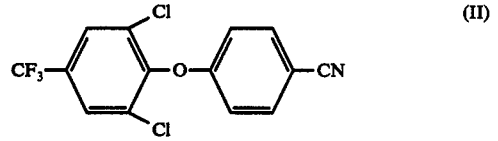

preferably in a weight ratio from about 1:0.05 to 1:10. The composition can be used as a total herbicide or, at suitable levels of application, in growing crops as a selective herbicide against particularly resistant weeds.

10 Claims, No Drawings

HERBICIDAL COMPOSITION OF PARTICULAR TRIAZINONE AND DIPHENYL ETHER

The present invention relates to new herbicidal synergistic combinations of a known 1,2,4-triazin-5-one and a known substituted diphenyl ether.

It has been disclosed in U.S. Pat. No. 3,671,523 that 1,2,4-triazin-5-ones, for example 4-amino-6-tert.-butyl-3-methylthio-1,2,4-triazin-5-one, can be used as herbicides. Further, it is known from U.S. Pat. No. 3,954,829 that substituted diphenyl ethers, for example 2,6-dichloro-4-trifluoromethyl-4'-cyano-diphenyl ether, can be employed as herbicides. The herbicidal activity of the above-mentioned compounds, however, sometimes is less than might be desired, especially in the case of weeds which are difficult to combat.

The present invention now provides a herbicidal composition containing as active ingredients (1) 4-amino-6-tert.-butyl-3-methylthio-1,2,4-triazin-5-one, of the formula

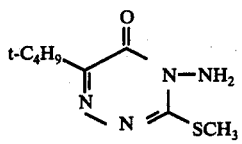

and (2) 2,6-dichloro-4-trifluoromethyl-4'-cyano-diphenyl ether, of the formula

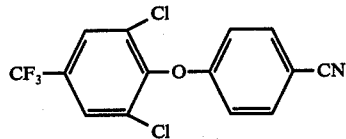

alone or in admixture with a solid or liquid or liquefied gaseous diluent or carrier.

The invention also provides a method of combating weeds which comprises applying to the weeds, or to a habitat thereof, a composition according to the present invention.

Surprisingly, the activity of the active-compound combination according to the invention is substantially greater than the sum of the actions of the individual active compounds. An unforeseeable genuine synergistic effect is concerned, not merely a supplementation of the action. The active-compound combination accordingly represents a valuable enrichment of the art.

The active compounds contained in the active-compound combination according to the invention are already known (see U.S. Pat. No. 3,671,523 and German Offenlegungsschrift (German Published Specification) No. 2,333,848).

The synergistic effect manifests itself particularly strongly at certain combination ratios. However, the weight ratios of the active compounds in the active-compound combination can fluctuate within relatively wide ranges. In general, about 0.05 to 10 parts by weight, preferably about 0.1 to 5 parts by weight, of the active compound of the formula (II) are used per part by weight of the active compound of the formula (I).

The active compound combination according to the invention exhibits a very good action against weeds and wild grasses without damaging various crops. It can therefore be used for the selective combating of weeds in such cultures. When used in higher amounts, the combination according to the invention is also suitable for the total combating of weeds.

Weeds which can be combated are in particular:

dicotyledon weeds such as: mustard (Sinapis), cress (Lepidium), bed straw (Galium), chickweed (Stellaria), camomile (Matricaria), mayweed (Anthemis), gallant soldier (Galinsoga), goosefoot (Chenopodium), annual nettle (Urtica), groundsel (Senecio), pigweed (Amaranthus), purslane (Portulaca), cocklebur (Xanthium), bindweed (Convolvulus), morning glory (Ipomoea), knotweed (Polygonum), sesbania (Sesbania), ragweed (Ambrosia), spear thistle (Cirsium), common thistle (Carduus), sow thistle (Sonchus), nightshade (Solanum), field cress (Rorippa), Rotala, false pimpernel (Lindernia), deadnettle (Lamium), speedwell (Veronica), mallow (Abutilon), Emex, thornapple (Datura), violet (Viola), hemp-nettle (Galeopsis), poppy (Papaver) and knapweed (Centaurea); and monocotyledon weeds such as barnyard grass (Echinochloa), foxtail (Setaria), wild millet (Panicum), crabgrass (Digitaria), timothy (Phleum), bluegrass (Poa), fescue (Festuca), goosegrass (Eleusine), signal grass (Brachiaria), ryegrass (Lolium), cheat (Bromus), oats (Avena), flatsedge (Cyperus), sorghum (Sorghum), quackgrass (Agropyron), Bermuda grass (Cynodon), Monocharia, Fimbristylis, arrowhead (Sagittaria), spikerush (Eleocharis), bulrush (Scirpus), paspalum (Paspalum), Ischaemum, gooseweed (Sphenoclea), crowfoot grass (Dactyloctenium), redtop (Agrostis), meadow foxtail (Alopecurus) and silky bent-grass (Apera).

The good activity of the active compound combination according to the invention against weeds which are difficult to combat, such as, for example, cleavers (*Galium aparine*), and against wild grasses which are difficult to combat, such as, for example, meadow foxtail (*Alopecurus myosuroides*) is to be singled out particularly. Millet-like wild grasses are also dealt with particularly well. It is a particular advantage that such weeds and wild grasses which are usually difficult to combat can be combated simultaneously with the active-compound combination according to the invention.

The active-compound combination of the invention can be employed as a selective herbicide in the following cultures:

dicotyledon cultures such as cotton (Gossypium), soya bean (Glycine), carrot (Daucus), bean(Phaseolus), pea (Pisum), potato (Solanum), flax (Linum), morning glory (Ipomoea), broad bean (Vicia), tomato (Lycopersicon) and groundnut (Arachis); and monocotyledon cultures such as rice (Oryzae), maize (Zea), wheat (Triticum), barley (Hordeum), oats (Avena), rye (Secale), sorghum (Sorghum), millet (Panicum), sugar cane (Saccharum), pineapple (Ananas), asparagus (Asparagus), and onion (Allium).

The active compound combination according to the invention is particularly suitable for the selective combating of weeds in cultures of potatoes, soy beans and corn.

However, the use of the active compound combination according to the invention is in no way restricted to these plants, or even to the stated genera, but extends in the same manner also to other plants.

Depending on the concentration, the combination can be used for the total combating of weeds, for example on industrial terrain and rail tracks, and on paths and squares with and without trees. Equally, the active compound combination can be used for combating weeds in perennial cultures, for example afforestations, decorative tree plantings, orchards, vineyards, citrus fruit plantations, nut orchards, banana plantations, coffee plantations, tea plantations, rubber plantations, oil palm plantations, cocoa plantations, soft fruit plantings and hopfields, and for the selective combating of weeds in annual cultures.

The active materials according to the instant invention can be utilized, if desired, in the form of the usual formulations or compositions with conventional inert (i.e., plant compatible or herbicidally inert) pesticide diluents or extenders, i.e., diluents, carriers or extenders of the type usable in conventional pesticide formulations or compositions, e.g., conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g., conventional pesticide surface-active agents, including emulsifying agents and-/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert disperisble liquid diluent carriers, including inert organic solvents, such as aromatic hydrocarbons (e.g., benzene, toulene, xylene, alkyl naphthalenes, etc.), halogenated, especially chlorinated, aromatic hydrocarbons (e.g., chlorobenzenes, etc.), cycloalkanes, (e.g., cyclohexane, etc.), paraffins (e.g., petroleum or mineral oil fractions), chlorinated aliphatic hydrocarbons (e.g., methylene chloride, dichlorofluoromethane, trichlorofluoromethane, chloroethylenes, etc.), alcohols (e.g., methanol, ethanol, propanol, butanol, glycol, etc.) as well as ethers and esters thereof (e.g., glycol monomethyl ether, etc.), amines (e.g., ethanolamine, etc.), amides (e.g., dimethyl formamide, etc.), sulfoxides (e.g., dimethyl sulfoxide, etc.), acetonitrile, ketones, (e.g., acetone, methyl ethyl ketone, methyl isobutyl ketone, cyclohexanone, etc.), and/or water; as well as inert dispersible finely divided solid carriers, such as ground natural minerals (e.g., kaolins, clays, alumina, silica, chalk, i.e., calcium carbonate, talc, attapulgite, montmorillonite, kieselguhr, etc.) and ground synthetic minerals (e.g., highly dispersed silicic acid, silicates, e.g., alkali silicates, etc.); whereas the following may be chiefly considered for use as conventional carrier vehicle assistants, e.g., surface-active agents, for this purpose: emulsifying agents, such as non-ionic and/or anionic emulsifying agents (e.g., polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active materials may be employed alone in the form of mixtures with one another or with such solid and/or liquid dispersible carrier vehicles and/or with other known compatible active agents, especially plant protection agents, such as other herbicides, or insecticides, acaricides, nematicides, fungicides, bactericides, rodenticides, fertilizers, growth-regulating agents, etc., if desired, or in the form of particular dosage preparations for specific application made therefrom, such as solutions, emulsions, suspensions, powders, pastes, and granules which are thus ready for use. Alternatively, they may be sold individually or as concentrates requiring tank mixing.

It has been found advantageous to employ oils, as extenders, especially petroleum fractions of paraffinic and/or naphthenic crude oils or oils of vegetable origin, such as soy bean oil, rape oil or olive oil.

As concerns commercially marketed preparations, these generally contemplate carrier composition mixtures in which the active material is present in an amount substantially between about 0.1–95% by weight, and preferably 0.5–90% by weight, of the mixture, whereas carrier composition mixtures suitable for direct application or field application generally contemplate those in which the active material is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g., a surface-active agent, such as an emulsifying agent and/or a dispersing agent, and an amount of the active material which is effective for the purpose in question and which is generally between about 0.0001–95%, and preferably 0.01–95%, by weight of the mixture.

The active materials can also be used in accordance with the well known ultra-low-volume process with good success, i.e. by applying such material if normally a liquid, or by applying a liquid composition containing the same, via very effective atomizing equipment, in finely divided form, e.g., average particle diameter of from 50–100 microns, or even less, i.e., mist form, for example by airplane crop spraying techniques. In this process it is possible to use highly concentrated liquid compositions with said liquid carrier vehicles containing from about 20 to about 95% by weight of the active material or even the 100% active substance alone, e.g., about 20–100% by weight of the active material.

The amounts used of the active compound combination according to the invention can be varied within a fairly wide range. In general, the amounts used are from 0.1 to 10 kg/ha, preferably from 0.2 to 5 kg/ha.

The active compound combination according to the invention can be applied both before and after the emergence of the plants. Preferably, it is used before the emergence of the plants, that is to say by the pre-emergence method.

Furthermore, the present invention contemplates methods of selectively killing, combating or controlling undesired vegetation, e.g., weeds, which comprises applying to at least one of correspondingly (a) such weeds, and (b) the corresponding habitat thereof, i.e., the locus to be protected, e.g., to a growing crop or to an area where a crop is to be grown, a correspondingly combative or toxic amount, i.e., a herbicidally effective amount, of the particular active material of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active material utilized in admixture with the carrier vehicle will depend upon the intended application. Therefore, in special cases it is possible to go above or below the aforementioned concentration ranges.

The good herbicidal action of the active compound combination can be seen from the biotest examples which follow. Whilst the individual active compounds exhibit weaknesses in their herbicidal action, the combination shows a very broad action against weeds and wild grasses, which goes beyond a simple summation of the actions.

A synergistic effect is involved in herbicides whenever the herbicidal action of the active compound combination is greater than that of the individually applied active compounds.

The action to be expected for a given combination of two herbicides can (see S. R. Colby, "Calculating synergistic and antagonistic responses of herbicide combinations," Weeds 15, pages 20-22, 1967) be calculated as follows:

If $X = \%$ damage by herbicide A when using $p$ kg/ha and $Y = \%$ damage by herbicide B when using $q$ kg/ha and $E$ = expected damage by herbicides A and B when using $p$ and $q$ kg/ha, then $E = X + Y - (X \cdot Y)/100$ If the actual damage is greater than calculated, the action of the combination is super-additive, that is to say a synergistic effect is concerned.

Tables I and II which follow show that the found herbicidal action of the active-compound combination according to the invention on the weeds is greater than the calculated action, that is to say a genuine synergistic effect is concerned.

EXAMPLE 1

Pre-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After 3 weeks, the degree of damage to the plants was determined in % damage in comparison to the development of the untreated control. The figures denoted:

0% = no action (like untreated control)
100% = total destruction

The active compounds, the amounts applied and the results can be seen from the tables which follow:

Table I

| Active compound or active compound combination | Amount used, kg/ha | Pre-emergence test/greenhouse % destruction | | | | | | |
|---|---|---|---|---|---|---|---|---|
| | | Soy beans | Potatoes | Corn | Galium aparine found* | cal-culated* | Alopecurus myosuroides found* | calculated* |
| (I) (known) | 0.1 0.4 | 0 0 | 0 0 | 0 0 | 0 0 | | 80 90 | |
| (II) (known) | 0.2 0.4 | 0 0 | 0 0 | 0 0 | 10 25 | | 10 20 | |
| (I) + (II) (combination according to the invention) | 0.1 + 0.2 = 0.3 | 0 | 0 | 0 | 70 | 10 | 100 | 82 |

*found = damage found
*calculated = damage calculated in accordance with the formula given earlier Table II

| Active compound or active compound combination | Amount used, kg/ha | Pre-emergence test/in the open % destruction | | |
|---|---|---|---|---|
| | | Potatoes | Galium aparine found* | cal-culated* |
| (I) (known) | 0.35 0.85 | 0 | 38 50 | |
| (II) (known) | 0.5 0.85 | 0 | 20 35 | |
| (I) + (II) (combination according to the invention) | 0.35 + 0.5 = 0,85 | 0 | 100 | 50.4 |

*found = damage found
*calculated = damage calculated in accordance with the formula given earlier It will be appreciated that the instant specification and examples are set forth by way of illustration and not limitation, and that various modifications and changes may be made without departing from the spirit and scope of the present invention.

What is claimed is:

1. A herbicidal composition consisting essentially of
   (1) 4-amino-6-tert.-butyl-3-methylthio-1,2,4-triazin-5-one of the formula

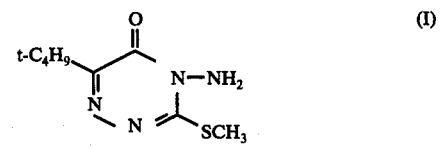

(I)

and (2) 2,6-dichloro-4-trifluoromethyl-4'-cyano-diphenyl ether of the formula

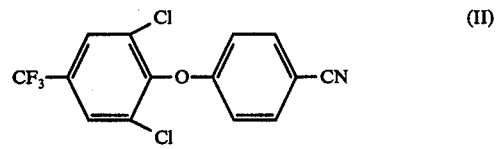

(II)

the weight ratio of the compound (I) to the compound (II) being between about 1:1.4 and 1:5.

2. A composition according to claim 1, in which the weight ratio of the compound (I) to the compound (II) is between about 1:1.4 and 1:2.

3. A composition according to claim 1, comprising about 0.1 to 95% by weight of compound (I) plus compound (II).

4. A composition according to claim 3, comprising at least about 5% by weight of at least one diluent or carrier selected from petroleum fractions of paraffinic and naphthenic crude oils and oils of vegetable origin.

5. A composition according to claim 3, comprising at least about 5% by weight of a liquid diluent or carrier containing a surface-active agent.

6. A composition according to claim 2, comprising about 5 to 99.9% by weight of at least one diluent or carrier selected from petroleum fractions of paraffinic and naphthenic crude oils and oils of vegetable origin, containing a surface active agent.

7. A method of combating weeds which comprises applying to the weeds, or to a habitat thereof, a composition according to claim 1.

8. A method according to claim 7, in which the composition is applied to an area of plant cultivation in a total amount of about 0.1 to 10 kg per hectare.

9. A method according to claim 8, in which the active ingredients are applied to an area of plant cultivation in a total amount of 0.2 to 5 kg per hectare.

10. A method according to claim 9, in which the composition is applied to an area of potato, soy bean or corn cultivation, and the composition comprises about 5 to 99.9% by weight of at least one diluent or carrier selected from petroleum fractions of paraffinic and naphthenic crude oils and oils of vegetable origin, containing a surface active agent.

* * * * *